(12) United States Patent
Inagaki (10) Patent No.: US 9,557,291 B2
(45) Date of Patent: Jan. 31, 2017

(54) SENSOR CONTROL DEVICE

(71) Applicant: NGK SPARK PLUG CO., LTD., Nagoya-shi, Aichi (JP)

(72) Inventor: Hiroshi Inagaki, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 198 days.

(21) Appl. No.: 14/481,306

(22) Filed: Sep. 9, 2014

(65) Prior Publication Data

US 2015/0068896 A1  Mar. 12, 2015

(30) Foreign Application Priority Data

Sep. 10, 2013  (JP) .................................. 2013-187252

(51) Int. Cl.
| | |
|---|---|
| *G01N 27/407* | (2006.01) |
| *G01N 27/416* | (2006.01) |
| *G01N 27/409* | (2006.01) |
| *G01N 27/419* | (2006.01) |

(52) U.S. Cl.
CPC ........ *G01N 27/4163* (2013.01); *G01N 27/409* (2013.01); *G01N 27/419* (2013.01)

(58) Field of Classification Search
CPC .... G01N 27/09; G01N 27/41; G01N 27/4065; F01N 2560/00–2560/0274
See application file for complete search history.

(56) References Cited

U.S. PATENT DOCUMENTS

| | | | |
|---|---|---|---|
| 4,932,238 A | 6/1990 | Yoshida et al. | |
| 6,295,862 B1 | 10/2001 | Kurokawa et al. | |
| 6,383,354 B1* | 5/2002 | Kurokawa ......... | G01N 27/4074 |
| | | | 204/406 |
| 6,442,998 B2 | 9/2002 | Kurokawa et al. | |
| 6,996,499 B2 | 2/2006 | Kurokawa et al. | |

(Continued)

FOREIGN PATENT DOCUMENTS

| | | |
|---|---|---|
| JP | 05-256817 A | 10/1993 |
| JP | 2624704 B2 | 6/1997 |

(Continued)

OTHER PUBLICATIONS

JPO computer-generated English language translation of JP 2624704 B2. Downloaded on May 31, 2016.*

(Continued)

*Primary Examiner* — Alexander Noguerola
(74) *Attorney, Agent, or Firm* — Sughrue Mion, PLLC (57) ABSTRACT

A gas sensor control device (2) includes a digital control unit (31) (CPU 91 in detail) functioning as a digital filter unit (99). Even when high-frequency noise components are superimposed on an electrical signal transmitted to a digital control unit (31) from the electromotive force cell (24), the high-frequency noise components are eliminated by the digital filter unit (99). Therefore, a terminal voltage Vs across both terminals of the electromotive force cell (24) generated according to oxygen concentration can be suitably extracted. The digital control unit (31) can suitably perform feedback control of the pump current Ip based on the terminal voltage Vs generated across both terminals of the electromotive force cell (24) while suppressing the influence of high-frequency noise components.

3 Claims, 5 Drawing Sheets

(56) References Cited

U.S. PATENT DOCUMENTS

| | | |
|---|---|---|
| 7,288,175 B2 | 10/2007 | Hada et al. |
| 8,257,565 B2 | 9/2012 | Kawase et al. |
| 2001/0039825 A1 | 11/2001 | Kurokawa et al. |
| 2004/0045824 A1 | 3/2004 | Hada et al. |
| 2004/0153258 A1 | 8/2004 | Kurokawa et al. |
| 2008/0196480 A1 | 8/2008 | Kawase et al. |
| 2014/0290337 A1 | 10/2014 | Higuchi et al. |

FOREIGN PATENT DOCUMENTS

| | | |
|---|---|---|
| JP | 2000-137018 A | 5/2000 |
| JP | 2000-329730 A | 11/2000 |
| JP | 2002-243700 A | 8/2002 |
| JP | 2004-93386 A | 3/2004 |
| JP | 2004-144733 A | 5/2004 |
| JP | 2008-8667 A | 1/2008 |
| JP | 2008-203142 A | 9/2008 |
| JP | 2014-190843 A | 10/2014 |

OTHER PUBLICATIONS

JPO computer-generated English language translation of JP-A-2008-8667. Downloaded Nov. 2, 2016.*
Communication dated Sep. 27, 2016 issued by the Japanese Patent Office in counterpart Japanese Patent Application No. 2013-187252.

* cited by examiner

SENSOR CONTROL DEVICE

BACKGROUND OF THE INVENTION

1. Field of the Invention

The preset invention relates to a sensor control device for controlling a sensor having a diffusion chamber, an electromotive force cell and a pump cell.

2. Description of the Related Art

Known sensors for linearly detecting oxygen over a wide concentration range within exhaust gas exhausted from an internal combustion engine include a diffusion chamber into which a gas to be measured (exhaust gas) flows through a diffusion rate controlling layer, and two cells, that is, an electromotive force cell (oxygen concentration measurement cell) provided with electrodes on a solid electrolyte layer and a pump cell (oxygen pump cell).

In order to maintain a detection voltage (Vs voltage) outputted from the electromotive force cell of this sensor to a predetermined value (target voltage value), a sensor control device is provided which is configured to perform feedback control of pump current supplied to the pump cell to thereby control the sensor.

However, a case may arise in that feedback control is not suitably performed due to factors such as variation in a characteristic of the sensor or use environment, and hence the pump current value becomes unsuitable. As a result, the detection voltage of the electromotive force cell does not converge to the target voltage value to thereby cause oscillation in the sensor control device performing feedback control.

In order to address this problem, a technique is known in which, for example, the inner side electrode of a pump cell and the detection electrode of an electromotive force cell are formed as a common electrode, and a leakage resistor having a small resistance value is added to the common electrode (see Patent Literature 1). Further, another technique is known in which a feedback resistor is added in parallel to the outer side electrode of a pump cell and the cell electrode of an electromotive force cell, and a voltage having the same phase as that of a pump current is superimposed on a Vs voltage to thereby suppress oscillation (see Patent Literature 2).

Furthermore, still another technique has been proposed in which a high-frequency component part of a pump current, obtained by eliminating low frequency components of a predetermined cut-off frequency or less from a pump current, is caused to flow to an electromotive force cell, thereby suppressing oscillation of a control circuit connected to a sensor (see Patent Literature 3).

[Patent Literature 1] Japanese Patent No. 2624704
[Patent Literature 2] JP-A-5-256817
[Patent Literature 3] JP-A-2002-243700

Problems to be Solved by the Invention

However, in causing a high-frequency component pump current to flow to the electromotive force cell, an instantaneous large current (spike current) also flows into the electromotive force cell according to the abrupt change of the pump current, whereby the electromotive force cell may be damaged.

For example, the pump current may change abruptly just after the pump current starts to flow such as just after activation of the sensor. In this case, since such an abrupt change in pump current is caused by the high frequency components, the high frequency components flow into the electromotive force cell. As a result, a spike current flows into the electromotive force cell, and hence the electromotive force cell may be damaged.

Accordingly, an object of the invention is to provide a sensor control device which, at the time of feedback-controlling a pump current based on a detection voltage, can suppress oscillation of the detection voltage without employing a configuration of causing a high-frequency component pump current to flow to an electromotive force cell.

SUMMARY OF THE INVENTION

The above object has been achieved by providing (1) a sensor control device for controlling a sensor, the sensor including a diffusion chamber into which gas to be measured flows through a diffusion rate controlling layer, an electromotive force cell which generates detection voltage according to concentration of a particular gas component within the diffusion chamber and a pump cell which pumps the particular gas component into or out of the diffusion chamber according to an externally supplied pump current, the sensor control device comprising: a control unit configured to feedback-control the pump current based on the detection voltage so that the detection voltage generated at the electromotive force cell approaches a target voltage; and a low pass filter unit configured to extract a predetermined low frequency component from the detection voltage, wherein the control unit feedback-controls the pump current based on the low frequency component extracted by the low pass filter unit.

The detection voltage generated in the electromotive force cell according to the concentration of the particular gas component is modified by the low pass filter unit to become a low frequency electrical signal which changes a small amount per unit time as compared with the voltage generated across both terminals of the pump cell by the pump current.

Thus, even when high-frequency noise components such as the voltage generated across the both terminals of the pump cell are superimposed on the detection voltage, the detection voltage and the high-frequency noise components can be separated by utilizing the difference of the frequency band therebetween. That is, the low frequency components extracted from the detection voltage by the low pass filter unit are free of high-frequency noise components, and hence are equivalent to "an actual detection voltage" generated in the electromotive force cell according to the concentration of the particular gas component.

Accordingly, when the control unit performs feedback control of the pump current based on the low frequency components extracted by the low pass filter unit, the pump current can be feedback-controlled based on an "actual detection voltage" while suppressing the influence of the high-frequency noise components.

As a result, the invention can suppress feedback control of the pump current to an unsuitable value, and the control unit can control the detection voltage to approach the target voltage and suppress oscillation of the detection voltage.

In other words, according to the invention, the detection voltage can be made to approach to the target voltage by feedback control of the pump current based on the low frequency components extracted by the low pass filter unit. This is done without employing a configuration of flowing to the electromotive force cell a pump current having high frequency components which is obtained by eliminating the low frequency components of a predetermined cut-off frequency or less from the pump current.

Thus, according to the invention, at the time of feedback-controlling the pump current based on the detection voltage, oscillation of the detection voltage can be suppressed without employing the configuration of flowing the high-frequency component pump current to the electromotive force cell. Incidentally, as the predetermined low frequency components set in the low pass filter unit, low frequency components in a range to which the sensor normally responds may be set in view of the configuration, etc., of the sensor. For example, the low frequency components extracted by the low pass filter unit may be set in a manner such that the phase of the frequency characteristic of the loop transfer function of the sensor and the sensor control device does not reach −180 degree in a frequency range where a gain is 0 dB or more, so as to suppress oscillation.

In a preferred embodiment (2), the sensor control device (1) further comprises a voltage analog-to-digital converter which converts the detection voltage generated at the electromotive force cell of the sensor to a digital value from an analog value, wherein the low pass filter unit performs a digital operation on the digital value of the detection voltage converted by the voltage analog-to-digital converter, to thereby extract the low frequency component, and the control unit feedback-controls the pump current by a digital process based on the digital value of the low frequency component.

In this manner, a configuration is provided in which the voltage analog-to-digital converter converts the detection voltage to a digital value from an analog value, and the low pass filter unit extracts the low frequency components by a digital operation. Thus, the low frequency components can be extracted from the detection voltage.

In another preferred embodiment (3), the sensor control device (1) further comprises a low-frequency analog-to-digital converter which converts the low frequency component extracted by the low pass filter unit to a digital value from an analog value, wherein the low pass filter unit is an analog circuit provided in a detection path of the detection voltage from the electromotive force cell to the control unit, and wherein the control unit feedback-controls the pump current by a digital process based on the digital value of the low frequency components converted by the low-frequency analog-to-digital converter.

In this manner, the low pass filter unit is configured as an analog circuit, and a low-frequency analog-to-digital converter is further provided which converts the low frequency component extracted by the low pass filter unit to a digital value from an analog value. Thus, the low frequency component can be extracted from the detection voltage.

Effects of the Invention

The invention can perform feedback control of the pump current based on a detection voltage generated by the electromotive force cell according to the concentration of a particular gas component while suppressing the influence of high-frequency noise components such as the voltage generated across both terminals of the pump cell. Thus, the detection voltage can be controlled to approach to the target voltage, and oscillation of the detection voltage can be suppressed.

According to the invention, at the time of feedback-controlling the pump current based on the detection voltage, oscillation of the detection voltage can be suppressed without employing a configuration of flowing a high-frequency component pump current to the electromotive force cell.

DESCRIPTION OF THE REFERENCE NUMERALS

Reference numerals used to identify various features in the drawings include the following.
1 internal combustion engine control system
2 gas sensor control device
8 gas sensor
14 pump cell
18 porous diffusion layer
20 diffusion chamber
24 electromotive force cell
31 digital control unit
91 central processing unit (CPU)
93 first A/D converter
94 D/A converter
97 second A/D converter
98 digital signal reception unit
99 digital filter unit
100 pump current control unit
101 second internal combustion engine control system
102 second gas sensor control device
111 low pass filter
121 second low pass filter
131 third low pass filter

DETAILED DESCRIPTION OF THE PREFERRED EMBODIMENTS

Hereinafter, preferred embodiments will be described in detail with reference to drawings. However, the invention should not be construed as being limited thereto.

1. First Embodiment 1-1. Entire Configuration

Figure 1:
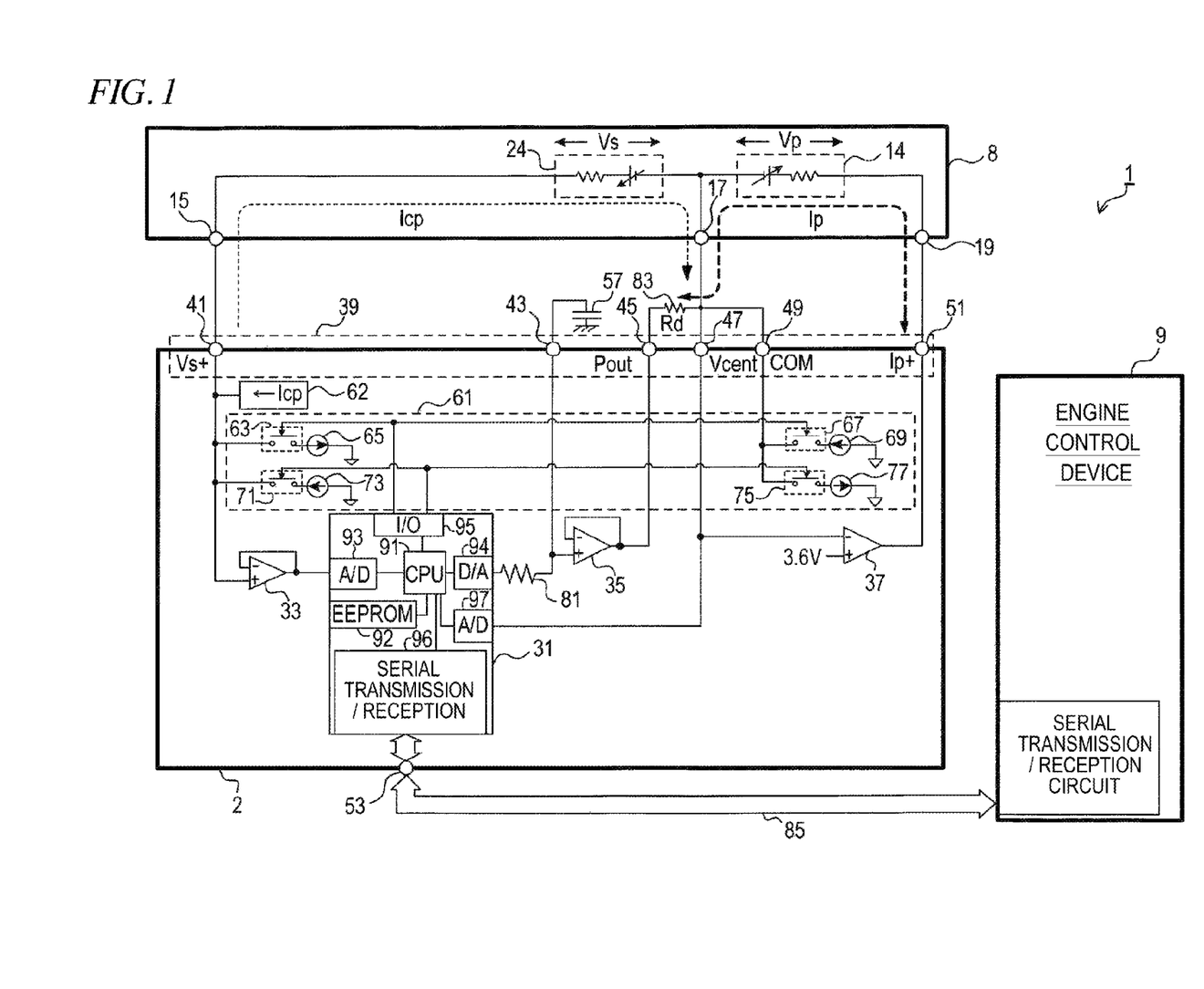
FIG. 1 is a diagram showing the entire configuration of a control system for an internal combustion engine including a gas sensor control device.

FIG. 1 shows the entire configuration of a control system 1 for an internal combustion engine including a gas sensor control device 2 as an embodiment to which the invention is applied.

The internal combustion engine control system 1 performs, for example, air-fuel ratio control, etc. of the internal combustion engine and is used for controlling the operational state of the internal combustion engine. The gas sensor control device 2 is used for detecting a particular gas component (oxygen in this embodiment) within the exhaust gas of the internal combustion engine.

The internal combustion engine control system 1 includes at least the gas sensor control device 2, a gas sensor 8 and an engine control device 9.

The gas sensor control device 2 detects a gas detection signal and an element resistance value signal from the gas sensor 8 provided in the exhaust pipe of the internal combustion engine (engine), and outputs the gas detection signal and the element resistance value signal to the engine control device 9 (engine CPU 9).

The gas sensor 8 linearly detects oxygen concentration over a wide range within the exhaust gas. The engine control device 9 controls the air-fuel ratio of the engine using the gas detection signal, as one of various kinds of control processing.

The gas sensor control device 2 includes a digital control unit 31 for executing the various kinds of control processing, a first operational amplifier 33, a second operational amplifier 35, a third operational amplifier 37, external connection terminals 39, a constant current output unit 61, a constant current source circuit 62, a serial communication terminal 53, etc.

The external connection terminals 39 include terminals (a Vs+terminal 41, a Pout terminal 45, a Vcent terminal 47, a COM terminal 49 and an IP+terminal 51) connected to the gas sensor 8 and a capacitor terminal 43 connected to a capacitor 57.

The constant current output unit 61 outputs a constant current for detecting the resistance value of the internal resistor of the gas sensor 8. The constant current source circuit 62 outputs a constant current (micro current Icp) to an electromotive force cell 24.

The serial communication terminal 53 transmits/receives various kinds of signals (gas detection signal, element resistance value signal, etc.) to/from the engine control device 9 via a serial communication cable 85.

Figure 2:
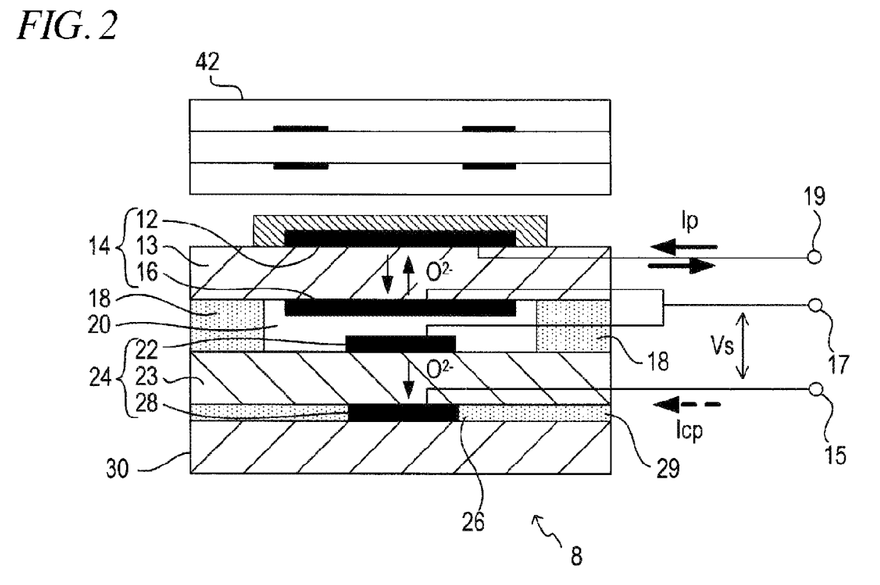
FIG. 2 is a diagram showing the schematic configuration of a gas sensor.

The schematic configuration of the gas sensor 8 will be shown in FIG. 2 and a brief explanation of the gas sensor will be made hereinafter.

The gas sensor 8 includes a pump cell 14, a porous diffusion layer 18, the electromotive force cell 24 and a reinforcing plate 30.

The pump cell 14 includes an oxygen-ion conductive solid electrolyte 13 made of partially stabilized zirconia ($ZrO_2$), and porous electrodes 12, 16 mainly made of platinum on major and rear surfaces of the solid electrolyte 13, respectively. The electromotive force cell 24 includes an oxygen-ion conductive solid electrolyte 23 made of partially stabilized zirconia ($ZrO_2$), and porous electrodes 22, 28 mainly made of platinum on major and rear surfaces of the solid electrolyte 23, respectively.

The porous electrode 16 of the pump cell 14 facing a diffusion chamber 20 and the porous electrode 22 of the electromotive force cell 24 facing the diffusion chamber 20 are electrically connected to each other and are connected to the sensor COM terminal 17 of the gas sensor 8. The sensor COM terminal 17 of the gas sensor 8 is connected to the Vcent terminal 47 and the COM terminal 49 of the gas sensor control device 2 and also connected to the Pout terminal 45 via a current detection resistor 83 (see FIG. 1).

The porous electrode 12 of the pump cell 14 is connected to the sensor Ip+terminal 19 of the gas sensor 8, while the porous electrode 28 of the electromotive force cell 24 is connected to the sensor Vs+terminal 15 of the gas sensor 8.

The sensor Ip+terminal 19 is connected to the IP+terminal 51 of the external connection terminals 39, while the sensor Vs+terminal 15 is connected to the Vs+terminal 41 of the external connection terminals 39 (see FIG. 1).

The reinforcing plate 30 is laminated on the electromotive force cell 24 via a reference chamber forming layer 29 so as to form a reference oxygen chamber 26 between the reinforcing plate and the electromotive force cell 24. The porous electrode 28 of the electromotive force cell 24 faces on the reference oxygen chamber 26.

The diffusion chamber 20 surrounded by the porous diffusion layer 18 is formed between the pump cell 14 and the electromotive force cell 24. In other words, the diffusion chamber 20 communicates with the measurement gas atmosphere via the porous diffusion layer 18. Although this embodiment employs the porous diffusion layer 18 formed by filling a void space with a porous material, it is possible to control the speed of the gas to be measured flowing into the diffusion chamber 20 by disposing small holes instead of the porous diffusion layer.

The gas sensor 8 includes a heater 42. The pump cell 14 and the electromotive force cell 24 are activated upon being heated by the heater 42 to thereby allow for gas detection.

Next, the oxygen concentration measurement operation of the gas sensor control device 2 will be described with reference to FIG. 1.

In the gas sensor control device 2, a pump current Ip flowing into the pump cell 14 is controlled so that a terminal voltage Vs generated across both terminals of the electromotive force cell 24 reaches a target voltage value (450 mV in this embodiment) while a constant micro current Icp is caused to flow to the electromotive force cell 24 from the constant current source circuit 62, thereby pumping oxygen into or out of the diffusion chamber 20.

Since the current value and the current flowing direction of the pump current Ip flowing through the pump cell 14 changes depending on the oxygen concentration (air-fuel ratio) of the exhaust gas, the oxygen concentration of the exhaust gas can be calculated based on the value of the pump current Ip. Incidentally, when the micro current Icp is caused to flow to the electromotive force cell 24 in a direction coincident with pumping oxygen out of the diffusion chamber 20 to the porous electrode 28 side, the reference oxygen chamber 26 acts as an internal oxygen reference source.

In the third operational amplifier 37 an inverting input terminal is connected to the Vcent terminal 47, a reference voltage (+3.6 V) is applied to a non-inverting input terminal, and an output terminal is connected to the sensor Ip+terminal 19 of the pump cell 14.

1-2. Digital Control Unit

Next, the digital control unit 31 will be explained.

The digital control unit 31 is configured by a known microcomputer having a CPU, an ROM, an RAM, etc. The digital control unit 31 according to this embodiment is configured to include a central processing unit 91 (hereinafter also called as a CPU 91), an EEPROM 92, a first A/D (analog-to-digital) converter 93, a D/A (digital-to-analog) converter 94, an I/O (input/output) unit 95, a serial transmission/reception unit 96, a second A/D converter 97, etc.

The central processing unit 91 (CPU 91) executes various kinds of operation control processing. The EEROM 92 is a storage unit which stores the contents of the various kinds of operation control processing and a parameter map, etc. The RAM (not shown) is a storage unit which temporarily stores control data, etc.

The A/D converter is a converter which converts an analog signal to a digital signal. The digital control unit 31 includes the first A/D converter 93 for subjecting the output voltage of the first operational amplifier 33 to an A/D conversion, and a second A/D converter 97 for subjecting the voltage at the Vcent terminal 47 to the A/D conversion.

The D/A converter is a converter which converts a digital signal to an analog signal. The digital control unit 31 includes the D/A converter 94 for subjecting the voltage to be outputted to the resistor 81 to a D/A conversion.

The I/O unit is an input/output unit for inputting and outputting a binary signal such as an ON signal and an OFF signal. The digital control unit 31 includes the I/O unit 95 for outputting a control command signal to the constant current output unit 61.

The serial transmission/reception unit 96 is a transmission/reception unit which performs serial communication according to a predetermined transmission protocol. In the digital control unit 31, the serial transmission/reception unit 96 transmits/receives a signal to/from at least the engine control device 9 by means of serial communication.

The digital control unit 31 (CPU 91 in detail) detects a voltage difference between the voltage at the sensor Vs+terminal 15 and the voltage at the Vcent terminal 47 (terminal voltage Vs generated across both terminals of the electromotive force cell 24), and feedback-controls the magnitude of the pump current Ip flowing to the pump cell 14 by PID control so that the electromotive force (terminal voltage Vs) of the electromotive force cell 24 becomes 450 mV. Concretely, the digital control unit 31 executes a PID operation based on a deviation ΔVs between the target voltage (450 mV) and the terminal voltage Vs of the electromotive force cell 24, and controls the output voltage of the second operational amplifier 35 so that the deviation ΔVs approaches 0 (in other words, the terminal voltage Vs approaches the target voltage), thereby controlling the pump current Ip flowing to the pump cell 14 from the third operational amplifier 37.

The pump current Ip flows toward the output terminal of the third operational amplifier 37 from the pump cell 14 or toward the pump cell 14 from the output terminal of the third operational amplifier 37 depending on polarity, that is, the positive or negative value thereof.

The digital control unit 31 (CPU 91 in detail) executes a multiplication operation between the magnitude of the pump current Ip calculated by the PID control and the resistance value Rd of the current detection resistor 83 to thereby detect the terminal voltage across the both terminals of the current detection resistor 83 as the gas detection signal (Vip signal). Then, the digital control unit 31 outputs a gas detection signal (Vip signal) to the engine control device 9 via the serial communication terminal 53.

The engine control device 9 calculates a corresponding oxygen concentration from a map (map representing a correlation between the gas detection signal and the oxygen concentration) stored therein, based on the gas detection signal (Vip signal). Further, the engine control device 9 performs a processing of detecting the air-fuel ratio based on the calculated oxygen concentration, and also performs an air-fuel ratio control processing so that the air-fuel ratio reaches a target air-fuel ratio.

1-3. Measurement Operation of Resistance Value (Temperature) of Electromotive Force Cell Next, a measurement operation of the internal resistance value Rpvs (temperature) of the electromotive force cell 24 of the gas sensor control device 2 will be described.

The constant current output unit 61 of the gas sensor control device 2 includes a first switch 63, a first constant current source circuit 65, a second switch 67, a second constant current source circuit 69, a third switch 71, a third constant current source circuit 73, a fourth switch 75 and a fourth constant current source circuit 77.

The first switch 63, the first constant current source circuit 65, the second switch 67 and the second constant current source circuit 69 are provided in order to flow an N pulse constant current (−I const) for detecting Rpvs of the electromotive force cell 24. The third switch 71, the third constant current source circuit 73, the fourth switch 75 and the fourth constant current source circuit 77 are provided in order to flow a P pulse constant current (+I const) for detecting Rpvs, which polarity is opposite that of the N pulse constant current for detecting Rpvs, to the electromotive force cell 24.

The digital control unit 31 of the gas sensor control device 2 is configured to store the digital value of the terminal voltage Vs of the electromotive force cell 24 in RAM (not shown) in the control processing of the CPU 91 to thereby sample and hold the terminal voltage Vs of the electromotive force cell 24.

That is, at the time of measuring the resistance value of the electromotive force cell 24, since a constant current is caused to flow to the electromotive force cell 24 from the constant current output unit 61, the terminal voltage Vs of the electromotive force cell 24 changes due to influence of the constant current. In contrast, when the digital control unit 31 samples and holds the terminal voltage Vs of the electromotive force cell 24 just before the start of flowing the constant current to the electromotive force cell 24 from the constant current output unit 61, the digital control unit 31 can perform PID control using the terminal voltage Vs just before measurement of the resistance value.

Further, the digital control unit 31 calculates a voltage difference ΔVr (=|Vs1−Vs2|) between a voltage Vs1 before the measurement and a voltage Vs2 upon measurement of the electromotive force cell 24. The voltage Vs1 before measurement is the terminal voltage Vs of the electromotive force cell 24 sampled and held before the start of flowing the constant current from the constant current output unit 61. The voltage Vs2 upon measurement is the terminal voltage Vs of the electromotive force cell 24 at the time of flowing the N pulse constant current (−I const) for detecting Rpvs. Since the voltage difference ΔVr is proportional to the resistance value of the internal resistance of the electromotive force cell 24, this voltage difference can be used as an element resistance value signal SRpvs representing the resistance value of the internal resistance of the electromotive force cell 24.

That is, the digital control unit 31 is configured, by calculating the voltage difference ΔVr, to enable output of the element resistance value signal SRpvs representing the value of the internal resistance of the electromotive force cell 24. Incidentally, the digital control unit 31 executes an Rpvs measurement processing in which the element resistance value signal SRpvs is obtained by dividing the voltage difference ΔVr by the current value of the N pulse constant current (−I const) for detecting Rpvs. The element resistance value signal SRpvs is proportional to the resistance value Rpvs of the internal resistance of the electromotive force cell 24 and is also proportional to the temperature of the electromotive force cell 24.

A constant time period is required until the terminal voltage Vs (voltage Vs2 upon the measurement) of the electromotive force cell 24 becomes stable after the N pulse constant current (−I const) for detecting Rpvs starts to flow. Thus, the digital control unit 31 performs the processing of detecting the terminal voltage Vs (voltage Vs2 upon measurement) of the electromotive force cell 24 after lapse of a stand-by time period for detecting Rpvs from the start of the N pulse constant current (−I const) flow for detecting Rpvs.

The digital control unit 31 (CPU 91 in detail) outputs the element resistance value signal SRpvs obtained by the Rpvs measurement processing to the engine control device 9 via the serial communication terminal 53.

The engine control device 9 controls the current supply to the heater 42 for heating the gas sensor 8 based on the element resistance value signal SRpvs so that a value correlating to the resistance value Rpvs of the internal resistor of the electromotive force cell 24 reaches a target value. This temperature control acts to maintain the temperature of the gas sensor 8 to a target value (for example, 800° C.) such that the current amount supplied to the heater 42 is reduced when the temperature of the electromotive force cell 24 is higher than a target value, while the current amount supplied to the heater 42 is increased when the temperature of the electromotive force cell 24 is lower than the target value.

1-4. Terminal Voltage Vs of Electromotive Force Cell

Next is a description of the effects obtained by executing a low-pass filter processing in the CPU 91 of the digital control unit 31, at the time of executing a control for controlling the terminal voltage Vs of the electromotive force cell 24 so as to approach the target voltage value.

Figure 3:
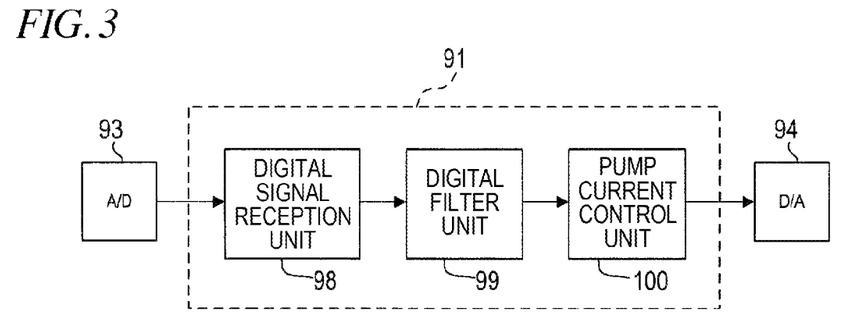
FIG. 3 is a functional block diagram of a control processing executed by the CPU of a digital control unit.

FIG. 3 is a functional block diagram of a control processing executed by the CPU 91 of the digital control unit 31 for controlling the pump current Ip based on the terminal voltage Vs of the electromotive force cell 24.

As shown in FIG. 3, the CPU 91 includes, as functional blocks, a digital signal reception unit 98, a digital filter unit 99 and a pump current control unit 100.

The digital signal reception unit 98 receives a digital signal which is an electrical signal transmitted to the first operational amplifier 33 via the Vs+terminal 41 from the electromotive force cell 24 and converted into a digital value from an analog value by the first A/D converter 93.

This digital signal contains a digital signal of the terminal voltage Vs generated by the electromotive force cell 24. The terminal voltage Vs generated by the electromotive force cell 24 according to the oxygen concentration is modified by the digital filter unit 99 to become a low frequency electrical signal which changes a small amount per unit time as compared with the voltage generated across both terminals of the pump cell 14 by the pump current Ip.

The digital filter unit 99 performs a digital processing as a low pass filter for extracting a signal of low frequency components equal to or lower than a predetermined cut-off frequency (150 Hz in this embodiment), from the digital signal received by the digital signal reception unit 98.

In this manner, the digital filter unit 99 extracts the electrical signal of the low frequency components equal to or lower than the cut-off frequency from the electrical signal transmitted to the first A/D converter 93 from the electromotive force cell 24 via the Vs+terminal 41 and the first operational amplifier 33. The low frequency components extracted by the digital filter unit 99 are inputted into the pump current control unit 100.

An example of a low pass digital filter for use in the present invention is described in US 2013/0054663, incorporated herein by reference in its entirety.

The pump current control unit 100 performs feedback control of the pump current Ip supplied to the pump cell 14, based on the low frequency components extracted by the digital filter unit 99, to thereby pump oxygen into and out of the diffusion chamber 20. Concretely, the low frequency components extracted by the digital filter unit 99 are taken as the terminal voltage Vs of the electromotive force cell 24, and the pump current Ip supplied to the pump cell 14 is subjected to PID control so that the low frequency components (terminal voltage Vs) approach the target voltage value to thereby pump oxygen into and out of the diffusion chamber 20.

According to the digital control unit 31 having the CPU 91 configured in this manner, even when high-frequency noise components such as the pump current Ip are superimposed on the electrical signal transmitted to the digital control unit 31 from the electromotive force cell 24 via the Vs+terminal 41 and the first operational amplifier 33, the digital filter unit 99 of the CPU 91 can eliminate these high-frequency noise components. Thus, the high-frequency noise components can be suppressed from entering the pump current control unit 100. In other words, since the CPU 91 functions as the digital filter unit 99, the terminal voltage Vs of the electromotive force cell 24 generated according to the oxygen concentration can be inputted into the pump current control unit 100 while eliminating the high-frequency noise components.

As a result, the digital control unit 31 can detect the terminal voltage Vs of the electromotive force cell 24 with high accuracy, and can also detect the oxygen concentration within the diffusion chamber 20 with high accuracy based on the pump current Ip. Thus, since the digital control unit 31 can suitably control the pump current Ip according to the actual oxygen concentration within the diffusion chamber 20, oscillation of the terminal voltage Vs can be suppressed.

1-5. Effects

As explained above, according to the internal combustion engine control system 1 of this embodiment, the gas sensor control device 2 includes the digital control unit 31 (CPU 91 in detail) which functions as the digital filter unit 99.

Thus, even when high-frequency noise components such as the pump current Ip are superimposed on the electrical signal transmitted to the digital control unit 31 from the electromotive force cell 24 via the Vs+terminal 41 and the first operational amplifier 33, these high-frequency noise components can be eliminated by the digital processing performed by the digital filter unit 99. Therefore, the terminal voltage Vs of the electromotive force cell 24 generated according to the oxygen concentration can be suitably extracted.

Accordingly, in the digital control unit 31 (CPU 91 in detail), the pump current control unit 100 can suitably perform feedback control of the pump current Ip based on the low frequency components extracted by the digital filter unit 99.

As a result, since the digital control unit 31 controls the pump current Ip to a suitable value based on the actual terminal voltage Vs generated in the electromotive force cell 24 according to the oxygen concentration within the diffusion chamber 20, the terminal voltage Vs can be controlled to approach to the target voltage value and oscillation of the terminal voltage Vs can be suppressed.

That is, the gas sensor control device 2 can cause the terminal voltage Vs to approach the target voltage value by feedback-controlling the pump current Ip based on the low frequency components extracted by the digital filter unit 99. This is done without employing a configuration of flowing to the electromotive force cell 24 a pump current having high frequency components which is obtained by eliminating the low frequency components of a predetermined cut-off frequency or less from the pump current Ip.

1-6. Corresponding Structure

The relation between those terms used to define the invention and corresponding structure in the first embodiment will next be described as follows.

The gas sensor control device 2 corresponds to an example of a sensor control device, the porous diffusion layer 18 corresponds to an example of a diffusion rate controlling layer, the exhaust gas corresponds to an example of gas to be measured, the oxygen corresponds to an example of a particular gas component, the terminal voltage Vs corresponds to an example of a detection voltage, and the gas sensor 8 corresponds to an example of a sensor.

Further, the digital control unit 31 corresponds to an example of a control unit, the CPU 91 for executing the function as the digital filter unit 99 corresponds to an example of a low pass filter unit, and the first A/D converter 93 corresponds to an example of a voltage A/D conversion unit.

2. Second Embodiment

Figure 4:
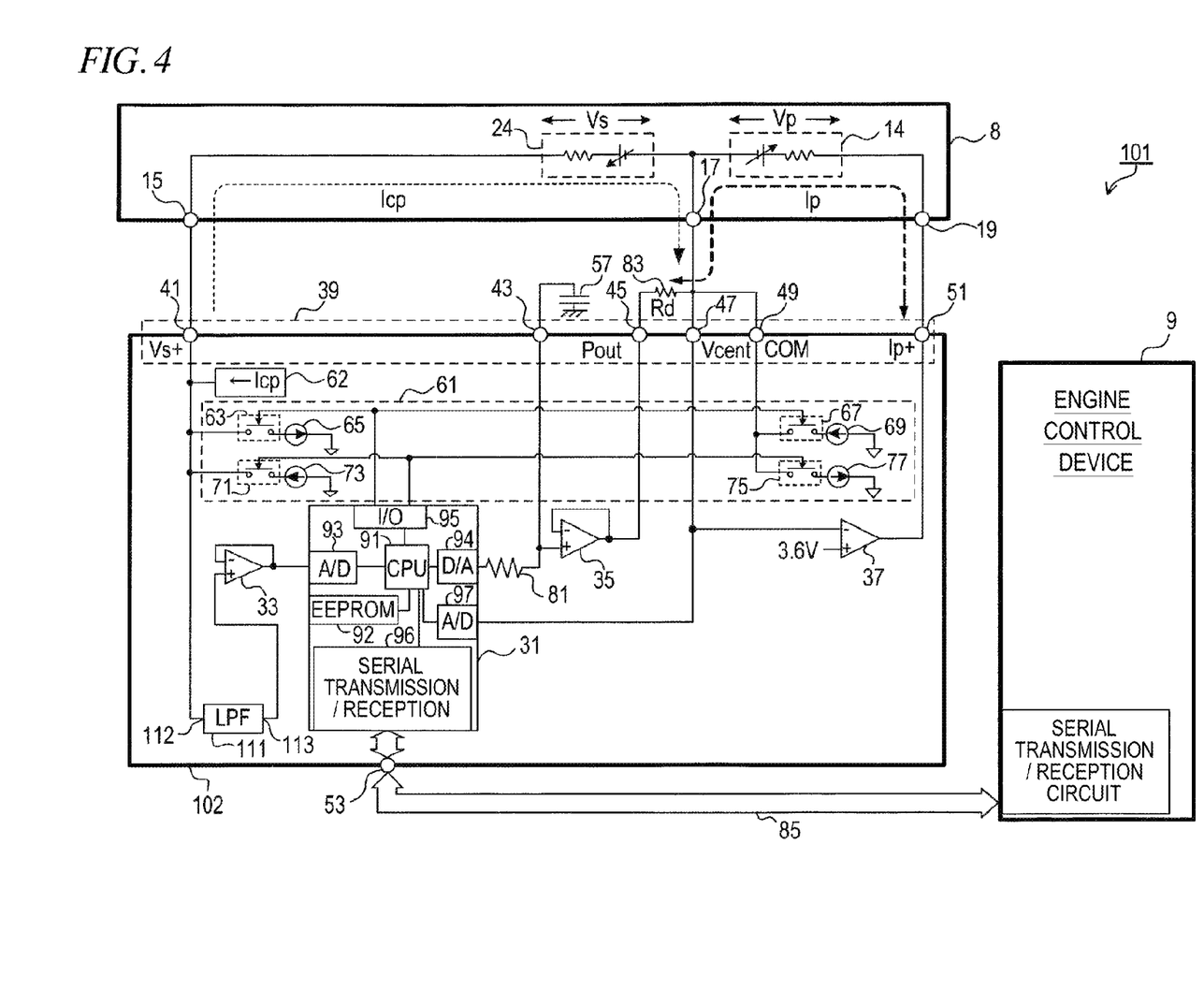
FIG. 4 is a diagram showing the entire configuration of a second internal combustion engine control system including a second gas sensor control device.

As a second embodiment, a second gas sensor control device 102 having a low pass filter 111 in the form of an analog circuit will next be described.

In the following explanation, portions of the second embodiment having the same configurations as those of the first embodiment are referred to by common symbols, respectively, with explanation thereof being omitted, and explanation will be made mainly as to portions of the second embodiment different from those of the first embodiment.

Figure 5:
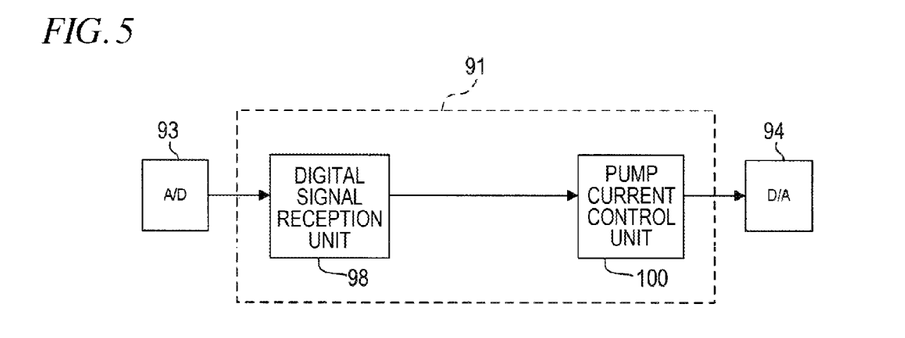
FIG. 5 is a functional block diagram of a control processing executed by the CPU of a digital control unit of the second embodiment.

FIG. 4 is a diagram showing the entire configuration of a second internal combustion engine control system 101 including the second gas sensor control device 102. FIG. 5 is a functional block diagram of a control processing executed by the CPU 91 of the digital control unit 31 in the second embodiment.

The second gas sensor control device 102 includes the digital control unit 31 for executing the various kinds of control processing, the first operational amplifier 33, a low pass filter 111, the second operational amplifier 35, the third operational amplifier 37, the external connection terminals 39, the constant current output unit 61, the constant current source circuit 62, the serial communication terminal 53 etc.

The hardware configuration of the second gas sensor control device 102 according to the second embodiment differs from the configuration of the gas sensor control device 2 of the first embodiment in that the low pass filter 111 is added. Further, the second gas sensor control device 102 differs from the configuration of the gas sensor control device 2 in that the digital filter unit 99 is omitted from the functional blocks of the CPU 91.

Next is an explanation of the effects of the low pass filter 111 (hereinafter also referred to as an LPF 111) at the time of executing control of the terminal voltage Vs of the electromotive force cell 24 so as to approach the target voltage value.

As shown in FIG. 4, the low pass filter 111 is provided in a path from the Vs+terminal 41 to the non-inverting input terminal of the first operational amplifier 33. The input terminal 112 of the low pass filter 111 is connected to the Vs+terminal 41, and the output terminal 113 of the low pass filter 111 is connected to the non-inverting input terminal of the first operational amplifier 33.

Figure 6:
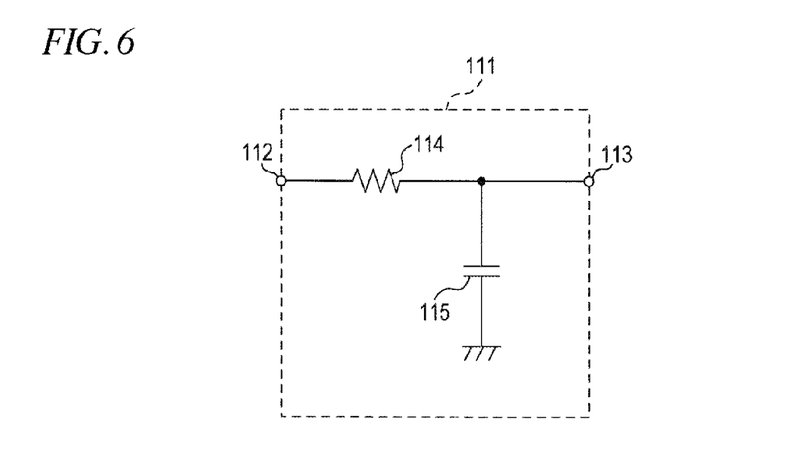
FIG. 6 is a circuit diagram of a low pass filter of the second embodiment.

FIG. 6 shows the circuit diagram of the low pass filter 111.

As shown in FIG. 6, the low pass filter 111 is configured by an analog circuit having a resistor element 114 and a capacitor 115. The resistor element 114 is connected between the input terminal 112 and the output terminal 113. The capacitor 115 is connected between the output terminal 113 and a ground line.

The resistance value of the resistor element 114 and the capacitance value of the capacitor 115 are selected so that the low pass filter 111 passes a signal of low frequency components equal to or lower than a predetermined cut-off frequency (150 Hz in this embodiment).

The terminal voltage Vs generated across both terminals of the electromotive force cell 24 according to the oxygen concentration is modified by the low pass filter to become a low frequency electrical signal which changes a small amount per unit time as compared with the voltage generated across both terminals of the pump cell 14 by the pump current Ip. The cut-off frequency of the low pass filter 111 is set in advance so as to pass the low frequency components of the terminal voltage Vs of the electromotive force cell 24 generated according to the oxygen concentration.

Thus, the electrical signal of the low frequency components equal to or lower than the cut-off frequency is extracted by the low pass filter 111 from the electrical signal transmitted to the non-inverting input terminal of the first operational amplifier 33 via the Vs+terminal 41 from the electromotive force cell 24, and is inputted to the digital control unit 31 via the first operational amplifier 33.

Accordingly, even when high-frequency noise components such as the pump current Ip are superimposed on the electrical signal transmitted to the digital control unit 31 from the electromotive force cell 24 via the Vs terminal 41 and the first operational amplifier 33, the low pass filter 111 can eliminate these high-frequency noise components. Thus, the high-frequency noise components can be suppressed from entering the digital control unit 31. That is, by providing the low pass filter 111, the terminal voltage Vs of the electromotive force cell 24 generated according to the oxygen concentration can be inputted into the digital control unit 31 while eliminating the high-frequency noise components.

As a result, the digital control unit 31 can detect the terminal voltage Vs of the electromotive force cell 24 with high accuracy and can also detect the oxygen concentration with high accuracy based on the pump current Ip. Thus, since the digital control unit 31 can suitably control the pump current Ip according to the actual oxygen concentration within the diffusion chamber 20, oscillation of the terminal voltage Vs due to the influence of noise, etc. can be suppressed. Further, the terminal voltage Vs of the electromotive force cell 24 can be made approach to the target voltage value.

2-2. Effects

As explained above, according to the second internal combustion engine control system 101 of the second embodiment, the second gas sensor control device 102 includes the low pass filter 111. Accordingly, even when high-frequency noise components are superimposed on the electrical signal transmitted to the digital control unit 31 from the electromotive force cell 24 via the Vs+terminal 41 and the first operational amplifier 33, the low pass filter 111 can eliminate the high-frequency noise components. Thus, the terminal voltage Vs of the electromotive force cell 24 generated according to the oxygen concentration can be suitably extracted.

Thus, the digital control unit 31 can perform feedback control of the pump current Ip based on the low frequency components extracted by the low pass filter 111.

As a result, since the digital control unit 31 controls the pump current Ip to a suitable value based on the actual terminal voltage Vs generated in the electromotive force cell 24 according to the oxygen concentration within the diffusion chamber 20, the terminal voltage Vs can be made approach to the target voltage value and oscillation of the terminal voltage Vs can be suppressed.

That is, the second gas sensor control device 102 can control the terminal voltage Vs so as to approach the target voltage value by feedback-controlling the pump current Ip based on the low frequency components extracted by the low pass filter 111. Further, this can be done without employing a configuration of flowing to the electromotive force cell 24 a pump current having high frequency components which is obtained by eliminating the low frequency components of a predetermined cut-off frequency or less from the pump current Ip.

2-3. Corresponding Structure

The relation between those terms used to define the invention and corresponding structure in the second embodiment will next be explained as follows.

The second gas sensor control device 102 corresponds to an example of the sensor control device, the porous diffusion layer 18 corresponds to an example of the diffusion rate controlling layer, the exhaust gas corresponds to an example of the gas to be measured, the oxygen corresponds to an example of the particular gas component, the terminal voltage Vs corresponds to an example of the detection voltage, and the gas sensor 8 corresponds to an example of the sensor.

Further, the digital control unit 31 corresponds to an example of a control unit, the low pass filter 111 corresponds to an example of a low pass filter unit, and the first AD converter 93 corresponds to an example of a low frequency A/D conversion unit.

3. Modifications

Although the above description is made as to specific embodiments according to the invention, the invention is not limited thereto and can be implemented in various modes within a range not departing from the gist of the invention.

For example, the cut-off frequency of the digital filter unit 99 and the low pass filter 111 is not limited to the aforesaid value, and each of the digital filter unit 99 and the low pass filter 111 may be configured so as to have a suitable cut-off frequency according to an object and/or usage, etc.

Figure 7:
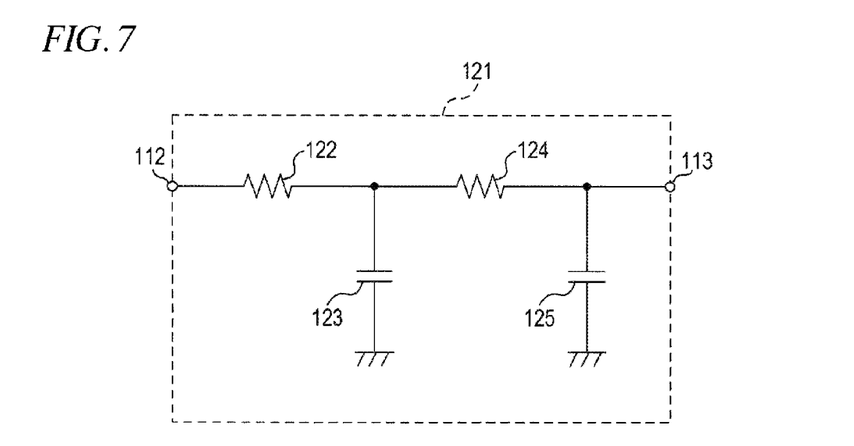
FIG. 7 is a circuit diagram of a second low pass filter.

Next, in the second embodiment, although the low pass filter 111 is configured by the single resistor element and the single capacitor element, a second low pass filter 121 configured by two resistor elements and two capacitor elements may be employed instead of the low pass filter 111.

FIG. 7 is an explanatory diagram showing the internal configuration of second low pass filter 121.

The second low pass filter 121 is configured by an analog circuit including a resistor element 122, a capacitor 123, a resistor element 124 and a capacitor 125.

A series circuit of the resistor element 122 and the resistor element 124 is connected between the input terminal 112 and the output terminal 113. The capacitor 123 has one end connected to a connection point between the resistor element 122 and the resistor element 124 and has the other end connected to a ground line. The capacitor 125 is connected between the output terminal 113 and the ground line.

The resistance values of the resistor element 122 and the resistor element 124 and the capacitance values of the capacitor 123 and the capacitor 125 are set so that the second low pass filter 121 passes a signal of low frequency components of a predetermined cut-off frequency or less.

The second low pass filter 121 thus configured can be used in place of the low pass filter 111 of the second embodiment.

Figure 8:
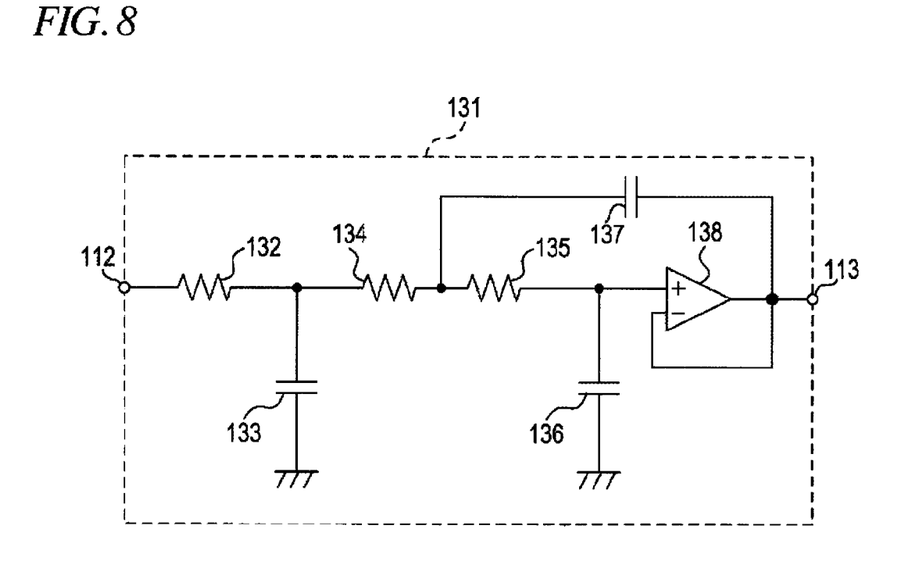
FIG. 8 is a circuit diagram of a third low pass filter.

Alternatively, a third low pass filter 131 as a positive feedback type low pass filter using an operational amplifier may be used in place of the low pass filter 111.

FIG. 8 is an explanatory diagram showing the internal configuration of the third low pass filter 131.

The third low pass filter 131 is configured by an analog circuit including a resistor element 132, a capacitor 133, a resistor element 134, a resistor element 135, a capacitor 136, a capacitor 137 and an operational amplifier 138.

A series circuit of the resistor element 132, the resistor element 134 and the resistor element 135 is connected between the input terminal 112 and the output terminal 113. The capacitor 133 has one end connected to a connection point between the resistor element 132 and the resistor element 134 and has the other end connected to a ground line. The capacitor 136 is connected between the non-inverting input terminal of the operational amplifier 138 and the ground line. The capacitor 137 has one end connected to a connection point between the resistor element 134 and the resistor element 135 and has the other end connected to the output terminal of the operational amplifier 138. The output terminal of the operational amplifier 138 is connected to the inverting input terminal thereof.

The resistance values of the respective resistor elements and the capacitance values of the respective capacitors are set so that the third low pass filter 131 passes a signal of low frequency components of a predetermined cut-off frequency or less.

The third low pass filter 131 thus configured can be used in place of the low pass filter 111 of the second embodiment.

In the digital control unit 31 of the second embodiment, a digital arithmetic circuit configured by a suitable hardware configuration of circuit elements may be employed in place of the central processing unit (CPU) 91. In this case, the magnitude of the pump current Ip flowing to the pump cell 14 may be subjected to PID control so that the electromotive force (terminal voltage Vs) of the electromotive force cell 24 becomes 450 mV, and a digital signal of the pump current Ip thus calculated may be outputted to the D/A converter 94. Further, in each of the first and second embodiments, the digital control unit 31 is provided with the serial communication terminal 53, and the gas detection signal (Vip signal) detected by the CPU 91 is outputted to the engine control device 9. However, each of the gas sensor control device and the second gas sensor control device may be configured such that the serial communication terminal 53 is omitted and also the detection processing of the gas detection signal (Vip signal) at the CPU 91 is omitted, and a terminal voltage across both terminals of the current detection resistor 83 is outputted to the engine control device 9.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2013-187252 filed on Sep. 10, 2013, incorporated herein by reference in its entirety.

What is claimed is:

1. A sensor control device for controlling a sensor, the sensor including a diffusion chamber into which a gas to be measured flows through a diffusion rate controlling layer, an electromotive force cell which generates a detection voltage according to concentration of a particular gas component within the diffusion chamber and a pump cell which pumps the particular gas component into or out of the diffusion chamber according to an externally supplied pump current, the sensor control device comprising:

a control unit configured to feedback-control the pump current based on the detection voltage so that the detection voltage generated at the electromotive force cell approaches a target voltage; and a low pass filter unit configured to extract a predetermined low frequency component from the detection voltage, wherein the control unit feedback controls the pump current based on the low frequency component extracted by the low pass filter unit.

2. The sensor control device as claimed in claim 1, further comprising a voltage analog-to-digital converter which converts the detection voltage generated at the electromotive force cell of the sensor to a digital value from an analog value, wherein the low pass filter unit performs a digital operation on the digital value of the detection voltage converted by the voltage analog-to-digital converter, to thereby extract the low frequency component, and the control unit feedback-controls the pump current by a digital process based on the digital value of the low frequency component.

3. The sensor control device as claimed in claim 1, further comprising a low-frequency analog-to-digital converter which converts the low frequency component extracted by the low pass filter unit to a digital value from an analog value, wherein the low pass filter unit is an analog circuit provided in a detection path of the detection voltage from the electromotive force cell to the control unit, and the control unit feedback-controls the pump current by a digital process based on the digital value of the low frequency component converted by the low-frequency analog-to-digital converter.

\* \* \* \* \*